United States Patent [19]

Harvey

[11] 4,100,790
[45] Jul. 18, 1978

[54] ELECTRONIC ORSAT FOR GAS ANALYSIS

[75] Inventor: Gerald J. Harvey, Westbury, N.Y.

[73] Assignee: William Printz Company, Inc., Westbury, N.Y.

[21] Appl. No.: 681,617

[22] Filed: Apr. 29, 1976

[51] Int. Cl.² .......................................... G01N 31/08
[52] U.S. Cl. ................................................ 73/23.1
[58] Field of Search ....................... 73/23.1, 422 GC; 23/232 C, 254 R

[56] References Cited

U.S. PATENT DOCUMENTS

| | | | |
|---|---|---|---|
| 3,071,005 | 1/1963 | Skidmore | 73/422 GC |
| 3,087,112 | 4/1963 | Pfefferle | 73/23.1 |
| 3,097,518 | 7/1963 | Taylor | 73/23.1 |
| 3,134,257 | 5/1964 | Reinecke | 73/23.1 |
| 3,385,101 | 5/1968 | Roof | 73/23.1 |
| 3,451,255 | 6/1969 | Neville | 73/23.1 |
| 3,626,761 | 12/1971 | Haruki | 73/422 GC |
| 3,772,909 | 11/1973 | Anderson | 73/23.1 |

OTHER PUBLICATIONS

Perkin–Elmer Publication, "Vapor Fractometry (Gas Chromatography", 1958 p. 22.

Primary Examiner—Richard C. Queisser
Assistant Examiner—Stephen A. Kreitman
Attorney, Agent, or Firm—Louis Weinstein

[57] ABSTRACT

Method and apparatus for detecting the presence and proportional amounts of constituents in an unknown gaseous sample. A carrier gas urges the sample through a column containing an adsorption material, which passes known constituents of the gas sample therethrough at predetermined time intervals. The carrier gas and separated constituents are passed over separate temperature sensitive elements to derive a signal representative of the proportion of the constituent being separated at any given time interval. A recorder plots a curve of percentage of concentration constituent versus time, wherein the peaks of the curve represent the particular constituents of the sample.

Utilizing air as the carrier, the percentage of nitrogen ($N_2$) and oxygen ($O_2$) may be determined through the use of a percentage $N_2 - O_2$ curve. Means are also provided for determining the temperature of the sample.

1 Claim, 10 Drawing Figures

FIG. 5. CURVE OF NITROGEN/OXYGEN RATIO VS. PEAK HEIGHT

ELECTRONIC ORSAT FOR GAS ANALYSIS

BACKGROUND OF THE INVENTION

The present invention relates to a novel method and apparatus for gas analysis, and more particularly to a novel electronic orsat for accurate qualitative and quantitative gas analysis especially adapted for determining concentration of $N_2$ and $O_2$ in a sample gas.

Gas chromatography is one of the most popular methods of instrument analysis, as a result of the fact that quantitative and qualitative results can be obtained with maximum ease and reliability. Gas chromatography may be defined as the qualitative and quantitative separation and detection of a mixture of gases and/or vapors by injecting a mixture into a stream of carrier gas that passes over either an adsorptive or solvent surface, usually coated upon a fixed phase, that permits each component to flow at a speed proportional to its relative affinity for the carrier as compared to the fixed phase. Separated components are detected as they emerge by some physical or chemical change in the carrier gas with the component mixed into it.

BRIEF DESCRIPTION OF THE PRESENT INVENTION

The electronic gas analyzer of the present invention is characterized by providing an extremely simple and yet effective gas sample injection system having high reliability and a wide variety of both laboratory and field applications.

The instrumentation is adapted to facilitate rapid analysis of the sample while providing inherent accuracy which is better than twice that of conventional techniques (1% compared to 2% for mechanical devices), such as, for example, orsat analyzers.

In the apparatus of the present invention the gaseous sample is inserted into a sample tube. The carrier gas is introduced under pressure into the sample tube to pass the gaseous sample through a temperature controlled column containing a selected adsorptive material retained within the column by a fixed phase material. The gaseous sample is passed over a temperature sensitive element simultaneously with the passage of the carrier gas over a second temperature sensitive element similar to the first temperature sensitive element. A recorder, coupled to the bridge comprising the temperature sensitive devices, records the bridge unbalance continuously against time, wherein the retention time of the constituent represents the qualitative analysis, while the proportion of the constituent in the sample is determined by peak height.

A novel and yet simple method for analyzing percentage of nitrogen ($N_2$) and oxygen ($O_2$) consists of utilizing the electronic analyzer described hereinabove with air as the carrier gas. In gaseous samples containing $O_2$ and $N_2$ in the same proportions as air, no peak will be observed in the plot at the retention time for oxygen-nitrogen. If there is less oxygen in relation to nitrogen, as compared to their proportions in air, then a positive peak will be observed. Conversely, if there is more oxygen in relation to nitrogen, as compared with their proportions in air, a negative peak will be observed. Establishing the peak height of a known sample, the actual peak height of the oxygen-nitrogen mixture may be converted into actual percentage of oxygen and nitrogen by converting the measured peak height into the actual percentage value in conjunction with a convenient chart provided therefor. The use of ambient air as a carrier is a much less expensive technique than those techniques conventionally employed, in which substantially pure helium, hydrogen or methane obtained from a commercial pressurized cylinder has normally been utilized as the carrier. Use of ambient air enables cylinder refill to be accomplished, literally, at a gas station air pump, so as to greatly facilitate the use of the equipment, especially as a portable device for field use.

It is therefore one primary object of the present invention to provide a novel electronic gas analyzer which accurately and reliably performs qualitative and quantitative analysis of gas samples in an automatic fashion.

Another object of the present invention is to provide a novel method and apparatus for determining the presence and proportion of oxygen and nitrogen in a gaseous sample, utilizing air as the carrier gas.

BRIEF DESCRIPTION OF THE FIGURES

These as well as other objects of the present invention will become apparent when reading the accompanying description and drawing, in which.

DETAILED DESCRIPTION OF THE INVENTION

As is well known in the field of gas chromatography, constituents of a gaseous sample are separated by an adsorptive material such that the peak values of the constituents arrive at the detector means at different predetermined time intervals. The time elapsed from the injection of the mixture into the stream to the arrival of the peak of the detector is commonly referred to as the retention time. Under any given set of conditions — that is, column temperature, carrier gas flow rate, fixed phase conditions — the retention time for any given component will always be the same, and, in the case of major fixed gas components, no overlapping occurs so long as the proper column and carrier are selected. It is further known that the concentration of the constituent in a gaseous sample is directly proportional to the peak height of the constituent as measured by the detector. The exact concentration is readily determined by multiplying the peak height of the concentration of the constituent within the unknown sample by the standard percentage of a known sample and dividing this value by the peak height reading derived for the known sample.

Figure 1:
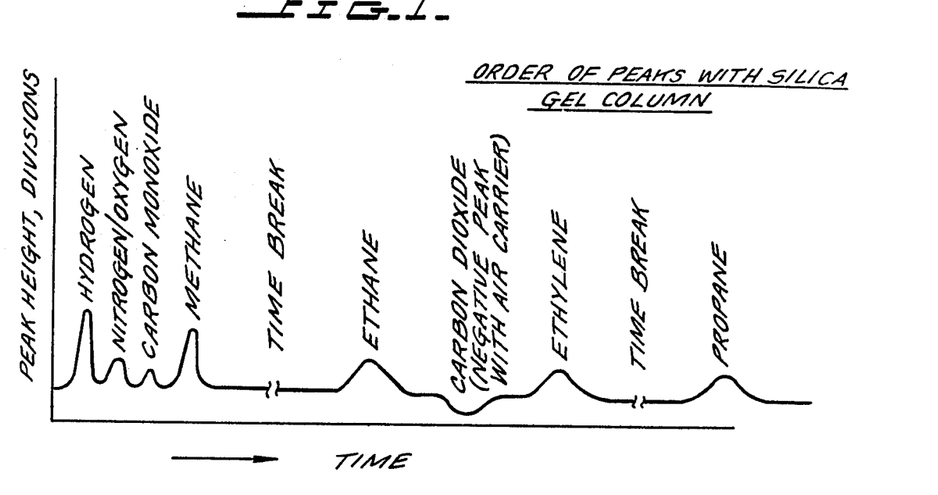
FIG. 1 is a plot showing the order of peaks obtained through electronic analysis, with said peaks being plotted against time.

FIG. 1 shows the peak height for different gaseous constituents when the sample is passed through a seven-foot length column containing silica gel. The standard curve shown in FIG. 1 is advantageous for use in the calibration procedure of such an electronic gas analyzer. Considering some typical constituents, the peak height for helium has a retention time of 20 – 30 seconds; nitrogen and oxygen 40 seconds; methane 1 minute; ethane 5 minutes; carbon dioxide 6 minutes to 6 minutes and 20 seconds; and propane 20 minutes and 20 seconds. Thus, with a knowledge of the retention time for various constituents a plot of the constituents contained within an unknown gas sample can be very accurately analyzed qualitatively.

It should be noted that certain constituents provide negative peaks. For example, carbon dioxide develops a negative peak when analyzed utilizing air as the carrier.

Figure 2:
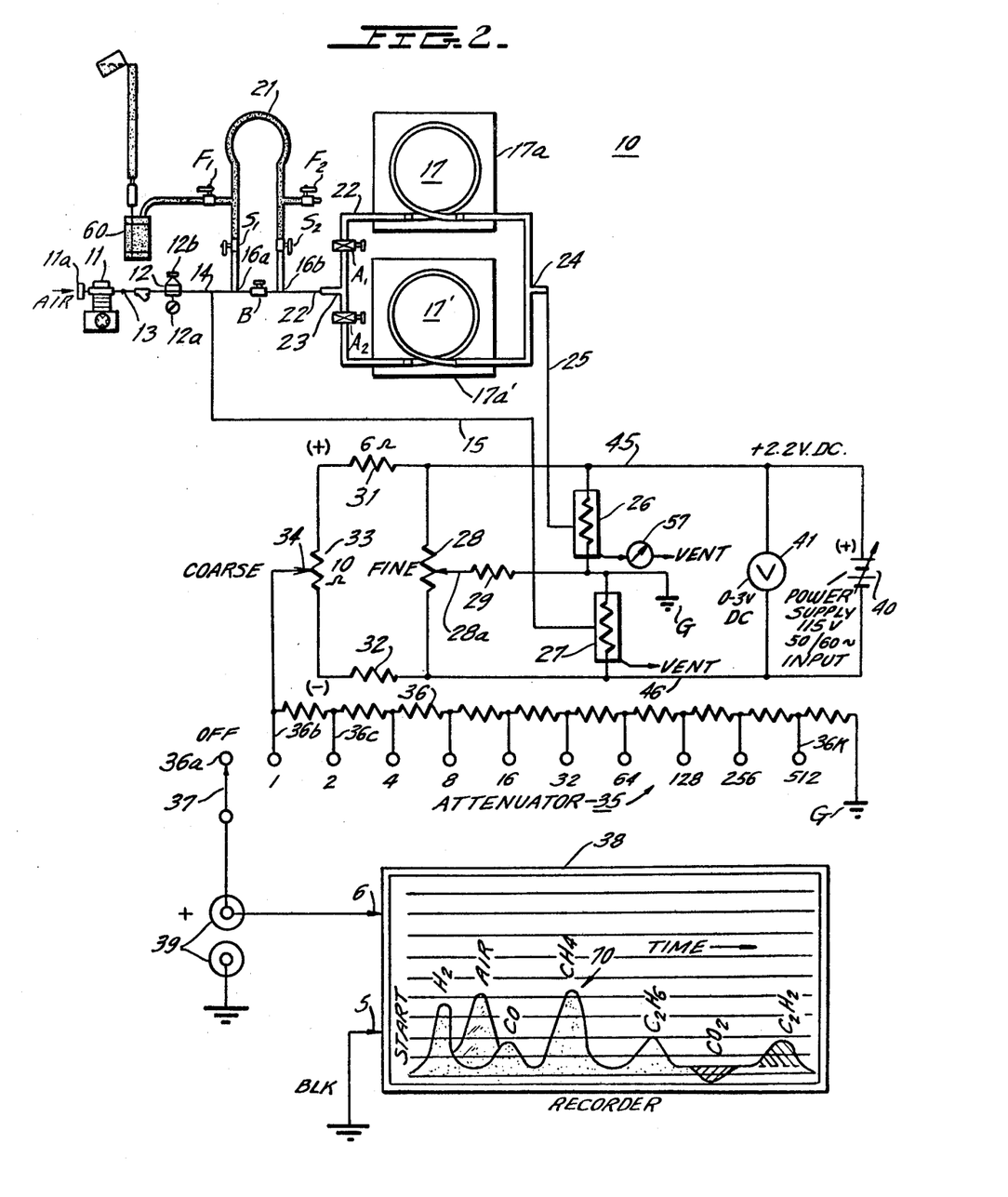
FIG. 2 is a schematic diagram showing an electronic gas analyzer designed in accordance with the principles of the present invention.
Figure 2A:
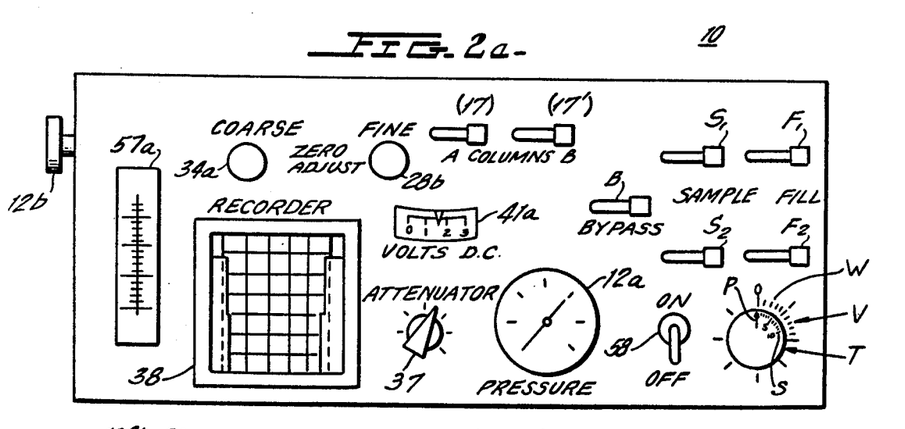

FIGS. 2 and 2a show the electronic gas analyzer and the front panel of the analyzer equipment in which the analyzer 10 is comprised of a storage tank 11 which is filled with the carrier gas injected into the tank under pressure, preferably to a minimum value of 40 psi, said carrier gas being injected at an input 11a. Tank 11 is coupled through conduit 13 to a regulator valve 12 and accompanying pressure gauge 12a, which gauge is also shown as being mounted on the front panel depicted in FIG. 2a. Adjustment of the pressure may be accomplished through the use of a control knob 12b, which may be mounted along one side of the unit (See FIG. 2a). The output of regulator 12 is coupled through a T-connector 14 to a carrier gas conduit 15, to be more fully described, and a second T-connector 16a, whose output conduits are connected to a first valve $S_1$ and a second valve B, respectively. The opposite end of valve B is coupled to a T-connector 16b having a second arm thereof coupled to valve $S_2$ and to the input end of a dual column assembly, to be more fully described.

Valves $S_1$ and $S_2$ are coupled to a substantially U-shaped tube 21, commonly referred to as a sample tube, which is further coupled to valve $SF_1$ and $F_2$ respectively provided for filling and purging the sample tube, in a manner to be more fully described.

T-connector 16b is connected through a conduit 22 to a T-connector 23 which, in turn, is coupled through valves $A_1$ and $A_2$ to the inputs of column assemblies 17 and 17', respectively. The outputs of these column assemblies are coupled through a T-connector 24 whose single output arm is connected through a conduit 25 into the input of an active filament assembly 26, to be more fully described.

Each of the column assemblies comprises an elongated tubular member, preferably of a ¼ inch outer diameter and formed of a suitable metal, such as, for example, stainless steel, aluminum or copper. The column is packed with an adsorptive material selected so as to determine fixed gas components at room temperature or volatile vapors at higher temperature. Suitable adsorptive materials are molecular sieves or 30–80 mesh silica gel. Obviously any other adsorptive material may be employed, depending, upon the particular fixed gas components to be detected. The column may be employed to operate at room temperature or at higher temperatures for detecting volatile vapors. The column is, therefore, contained within an insulated and temperature controlled housing 17a (and 17a') which may employ a water bath or constant temperature oven to obtain the necessary higher column temperatures. The adsorptive material is preferably held in the column by porous plugs or stranded wire.

The conduit 15 is coupled to a reference filament cell 27 which may, for example, contain a temperature sensitive semiconductive material. The active and reference filament assemblies 26 and 27 form first and second arms of an electrical bridge, whose third and fourth arms are comprised of an adjustable resistor 28, having an adjustable arm 28a, which, in turn, is connected through resistor 29 to the common terminal between the active and reference filaments and to ground potential G. A pair of resistors 31 and 32 are connected across adjustable resistance 28, and, in turn, have their opposite terminals connected to an adjustable resistor 33, whose adjustable arm 34 is connected to one end terminal of an attenuator 35, which comprises a resistance 36 having a plurality of taps 36a–36k, each of said taps being selectively engageable with a switch arm 37. The opposite terminal of tapped resistor 36 is coupled to ground potential G. The opposite terminal of movable switch arm 37 is coupled to the input 39 of a chart recorder 38, whose remaining input terminal is grounded. A pair of input sockets are provided for coupling accessory equipment to the recorder to make the recorder available for use in other applications.

A voltage source 40 is connected across the bridge in the manner shown. The voltage source is adjustable and is further provided with a voltmeter 41 connected across the terminals of the source to facilitate accurate adjustment of the output voltage.

Figure 3:
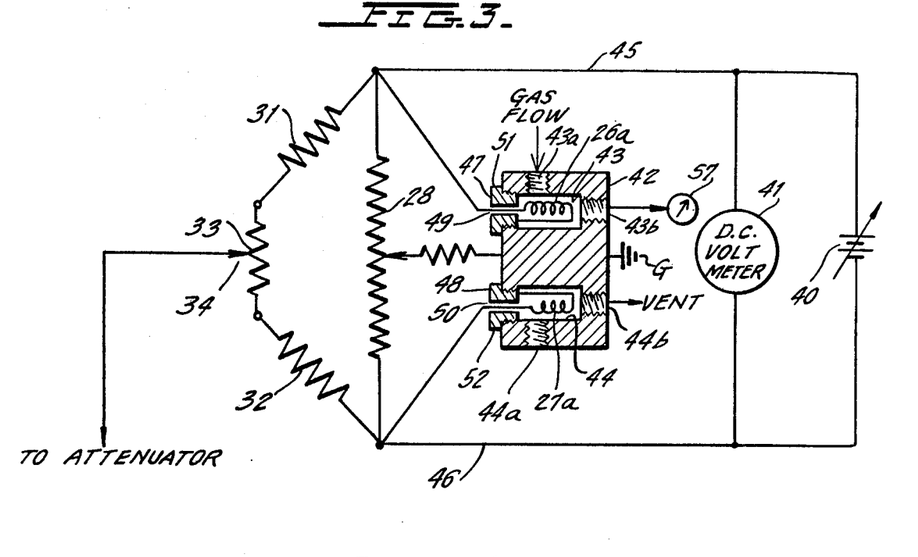
FIG. 3 is a schematic diagram showing the detector and bridge components of the system of FIG. 2 in greater detail.

FIG. 3 shows a sectional view of the active filament elements as comprising a conductive detector block 42, coupled through a suitable lead to ground potential G. The conductive block is provided with a pair of cavities 43 and 44, which receive the filament assemblies comprised of filaments 26a and 27a, each having a first terminal connected to leads 45 and 46, respectively, of the bridge circuit which leads extend through sealing plugs 47 and 48 provided with insulating means 49 and 50 to respectively electrically insulate the filament members from the conductor plugs and the detector block. O-rings 51 and 52 are provided to air-tightly seal the threaded couplings between detector block 42 and the sealing plugs 47 and 48. Each of the cavities 43 and 44 are provided with tapped input openings 43a and 44a, respectively, for threadedly receiving suitable coupling members (not shown, for purposes of simplicity), which air-tightly couple conduits 25 and 15 to the respective cavities. The cavities are further provided with tapped output openings 43b and 44b, respectively, to couple the gas flow respectively to gauge 57 and a vent. The flow meter 57, shown in FIG. 2, is also comprised of a visually observable gauge 57a, shown in FIG. 2a, in which the flow rate of the carrier gas-sample gas mixture to cavity 43 may be obtained. For example, the flow rate for the analyses set forth hereinabove should preferably be adjusted so that the flow through the active filament chamber is 100 cc/min. If desired, the openings of cavity 44 may be left open to communicate with surrounding air at ambient temperature instead of being coupled to the carrier gas supply.

Figure 4:
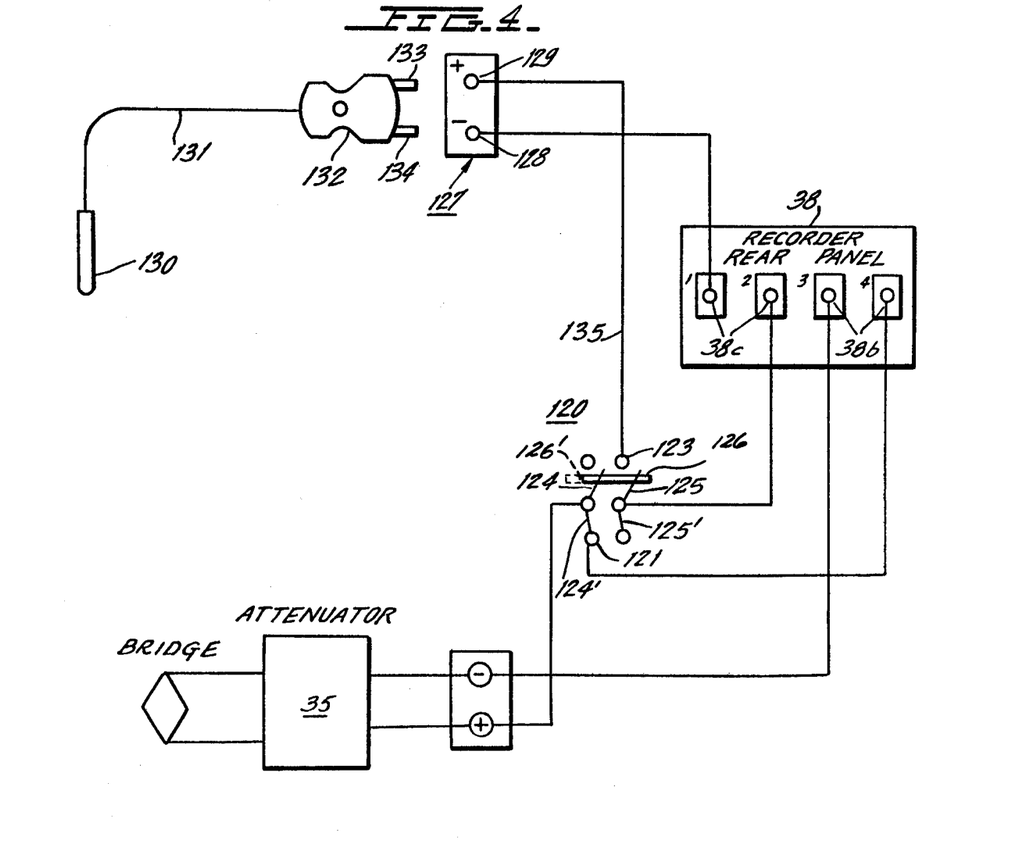
FIG. 4 is a schematic diagram showing the manner in which a thermocouple may be combined with the electronic gas analyzer.

As shown in FIG. 4, the versatility of the equipment may be enhanced by providing switch means adapted for connecting a thermocouple device to the recorder to permit a plot of temperature readings to be obtained. As shown in FIG. 4, recorder 38 is provided with a first pair of input terminals 38b respectively connected to one stationary contact 121 of a switch assembly 120 and one terminal of attenuator 35. The remaining pair of terminals 38c are respectively coupled to one terminal 128 of a receptacle 127 and to one movable arm 125 of switch assembly 120. Switch assembly 120 is comprised of a pair of movable arms 124 and 125 mechanically ganged together by a mechanical link 126 and movable to a first solid line position 126 and to a second dotted line position designated by the numerals 126'.

The thermocouple probe 130 is coupled through a lead 131 to a male plug assembly 132. Lead 131 may be of any desired length so as to facilitate insertion of the thermocouple into a chamber or other device whose temperature is to be measured. For example, the thermocouple may be inserted into a flue to record flue temperature in conjunction with an analysis of flue gas, which may be performed either before or after obtaining temperature readings. Male plug 132 is provided with prongs 133 and 134 which may be releasably inserted in the female sockets 129 and 128 respectively to connect the thermocouple into the circuit. In applications wherein temperature readings are to be taken, the double-pole-double-throw switch assembly 120 is moved to the solid line position, establishing an electrical path from prong 133 of male plug 132 through socket 129, lead 135, stationary contact 123 and movable contact arm 125 to one of the pair of input terminals 38c provided in the recorder 38. The remaining socket 128 of receptacle 127 is permanently electrically connected to the remaining terminal of the terminal pair 38c.

In order to perform quantitative and qualitative analysis upon a gas sample, the switch assembly 120 is moved to the dotted line position, establishing an electrical path from the positive terminal of the attenuator circuit through movable switch arm 124 (in the position 124') and stationary contact 121 to one of the pair of terminals 38b. The remaining terminal of the terminal pair 38b is permanently wired to the positive terminal of the attenuator circuit.

Making reference to FIGS. 2, 2a and 3, the operation of the electronic gas analyzer is as follows:

Storage tank 11 is pressurized to a predetermined pressure, preferably 40 psi. The power control switch 58 provided on the front panel of the device (FIG. 2a) is turned to the ON position.

The output voltage of power supply 40 should lie within the range from 2.0 to 2.4 volts, which reading appears on the dial face 41a of voltmeter 41 (See FIG. 2a). The power supply should preferably be adjusted to obtain a reading of 2.2 volts.

With the switch arm 37 connected to the OFF terminal 36a of attenuator 35, the galvanometer (not shown) provided in recorder unit 38 should be set to a mechanical zero reading. The desired attenuator setting (i.e., with movable arm 37 being coupled to one of the stationary taps 36a through 36k) is then selected. Electrical zero adjustment is then obtained by adjustment of the coarse and fine adjustment control knobs 34a and 28b, which are mechanically linked to the resistor movable arms 34 and 28a respectively, shown in FIG. 2.

In order to run through an analysis, sample tube 21 must be filled. This is performed by operating the switch arms for the valves $F_1$, $F_2$, $S_1$, $S_2$, and B, which switch arms are provided in the upper right-hand region of the front panel, as shown in FIG. 2a. When the valves are closed, the switch arms are positioned substantially parallel to the front face of the panel. Opening of the valves is accomplished by drawing the switch arms directly outwardly, so that they are aligned substantially perpendicular to the front panel face. In order to fill the sample tube, switch arms $S_1$ and $S_2$ are closed, valve B is open, and valves $F_1$ and $F_2$ are opened. The sample tube is purged with the gaseous sample which may, for example, be contained within jar 60. The gas may be urged out of the sample jar by filling the jar with a liquid, such as, for example, water from a beaker, to inject the sample into sample tube 21. Once the sample tube is purged, valves $F_1$ and $F_2$ are closed by moving the valve arms provided on the front panel to the closed position (i.e., with the valve arms lying adjacent and parallel to the front panel face).

Valves $S_1$ and $S_2$ are then opened, and valve B is closed, causing the carrier gas to simultaneously flow through conduit 15 and through sample tube 21 into one of the columns 17 or 17' when tank 11 is connected to sample tube 21. The column selected is controlled by operation of the valves $A_1$ and $A_2$, wherein one of the valves is closed, while the other one is moved to the opened position. The switch arms for these valves also appear on the front panel (FIG. 2a).

Through the use of a gas standard such as natural gas or pure grade components, recorder 38 may be utilized to obtain retention times and reference peak heights during a first run thereof. After establishing retention times and reference peak heights for the equipment, the unknown sample may then be inserted into the sample tube 21, in a manner similar to that described hereinabove, in order to obtain a quantitative and qualitative analysis of the constituents within the unknown sample.

The catalytic combustion-thermal conductivity detector elements 26a and 27a operate, without adjustment or modification of any kind, by reacting to combustibles, such as hydrogen, carbon monoxide, methane, ethane, and so forth, and to non-combustibles such as oxygen, nitrogen, carbon dioxide and so forth, when air is employed as the carrier gas.

A column filled with silica gel separates fixed gas components in the order shown, for example, in FIG. 1. It should be noted that carbon dioxide develops a negative peak along the chart. The filaments may, for example, be formed of a temperature sensitive semi-conductor material. The difference in thermal conductivity of the component-carrier mixture pass through cavity 43, as compared with the carrier gas passed through cavity 44, upsets the electrical balance of the bridge (which has previously been nulled in the manner set forth hereinabove), thereby causing a current to flow into the recorder unit via attenuator 35. As alternative means, the chart recorder may be replaced by an ammeter or potentiometer, whose readings may be taken at predetermined intervals, such as, for example, every 5, 10 or 15 seconds. The use of platinum catalytic filaments enables larger responses to be obtained for combustible gases and vapors, enabling parts per million analyses to be performed. The attenuator 35 limits the current sent to the meter or recorder being employed, in order to keep responses on scale. In cases where readings go off-scale even after adjustment of the attenuator, sample size may be reduced to obtain readings within the capacity of the meter or recorder being employed.

Other special purpose detectors may be employed to obtain greater sensitivity or to detect components that cannot be detected either by thermal conductivity or catalytic combustion, which devices may include flame and radioactive ionization, infrared and other optical detector systems. Comparison of the retention times and peak values obtained during the analysis of a known gas as against the analysis performed for a sample gas yields the desired information. Retention time establishes the identity of the constituent, while peak height determines the percentage of that constituent relative to the total sample.

By dividing the peak height of an unknown component by the peak height of a known standard and multiplying this against the concentration of the known component, the concentration of the unknown component may be obtained. For example, if the concentration of a given component is 10%, represented by a peak height of 10 divisions on a galvanometer or potentiometer, and the same component in an unknown mixture yields a peak height of 20 divisions, the concentration of the unknown would be:

$$\text{Unknown Concentration} = \frac{\text{Peak Height of Unknown}}{\text{Peak Height of Standard}} \times \text{Standard\%} = \frac{20}{10} \times 10 = 20\%.$$

The electronic gas analyzer described hereinabove may be employed to determine percentage concentration of nitrogen and oxygen in a gaseous mixture using air as the carrier gas. The procedure of operation described hereinabove may be utilized to obtain nitrogen and oxygen concentration by inserting air under pressure into tank 11. The chromatographic column may be packed with silica gel, and a bridge detector is preferably equipped with catalytic combustion-thermal conductivity detector filaments 26a and 27a. Such a detector responds to the combustibles mentioned hereinabove when air is used as the carrier gas. If the gas mixture being analyzed contains oxygen and nitrogen in the same proportions as air ($N_2$ —79%:$O_2$ —21%), no peak will be observed at the retention time for oxygen-nitrogen. If there is less oxygen in relation to nitrogen, as compared to their proportions in air, then a positive peak will be observed, whereas when more oxygen is present as compared with the normal proportion of oxygen and nitrogen in air, a negative peak is developed.

Figure 5:
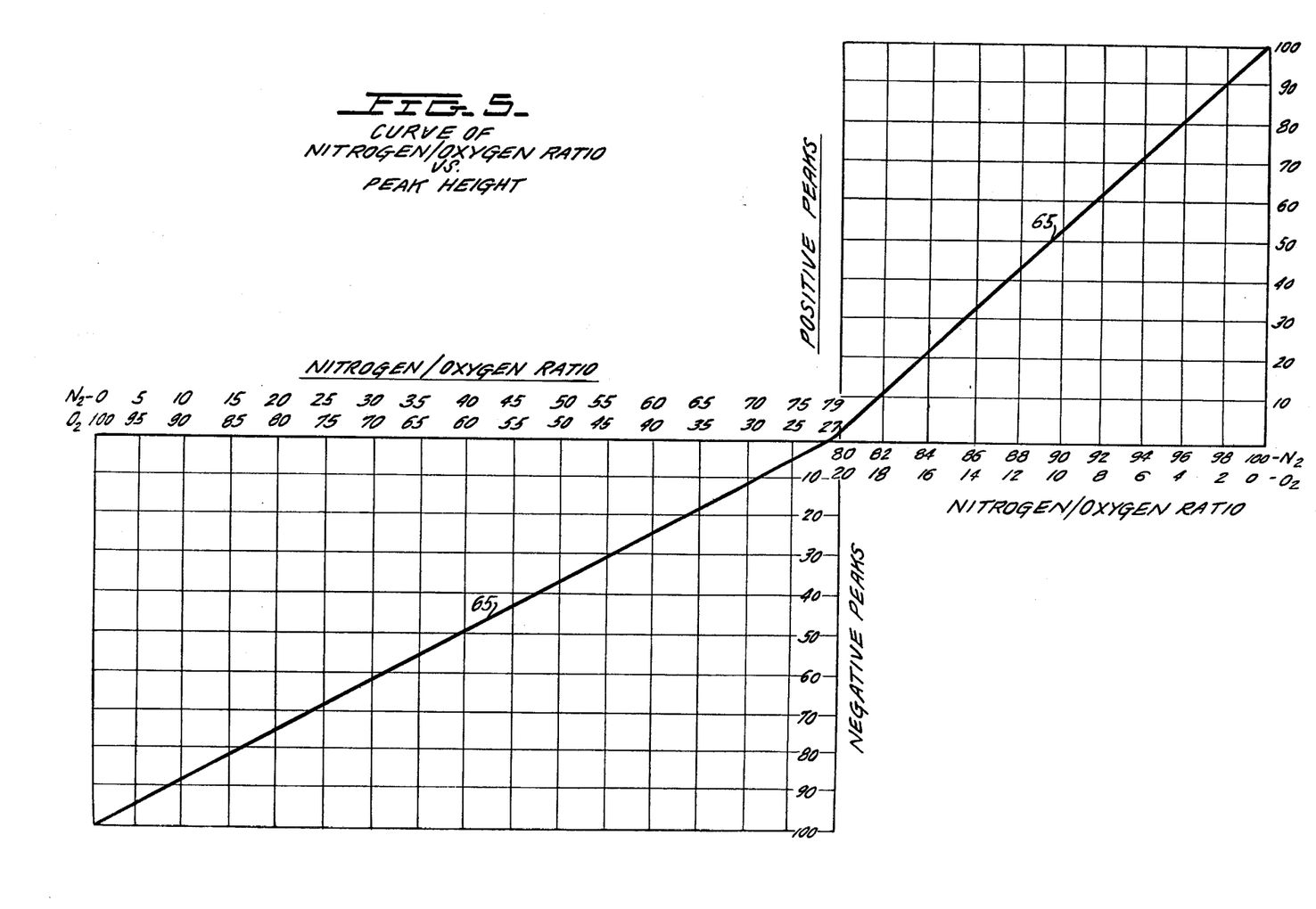
FIG. 5 is a plot showing a nitrogen-oxygen percentage ratio plotted against peak height, which may be used to great advantage in the qualitative and quantitative analysis of oxygen and nitrogen when air is utilized as the carrier gas.

FIG. 5 is a plot wherein the curve 65 shows the relationship between peak heights and divisions plotted along the vertical (positive and negative) axis, with nitrogen-oxygen concentration being plotted along the horizontal axis (the lower left-hand quadrant of the plot represents negative peaks (nitrogen deficiency), while the upper right-hand quadrant of the plot represents positive peaks (oxygen deficiency).

Since it is rather time-consuming to attempt to obtain 100 divisions to represent 100% nitrogen, the peak height is expressed as a percent of the peak height for 100% nitrogen. It therefore becomes a simple procedure to translate the actual peak height into percent of the 100% nitrogen peak height.

The procedure for determining oxygen and nitrogen concentration using air as the carrier gas is as follows. (Let it be assumed that other constituents are present in the sample gas).

Figure 6:
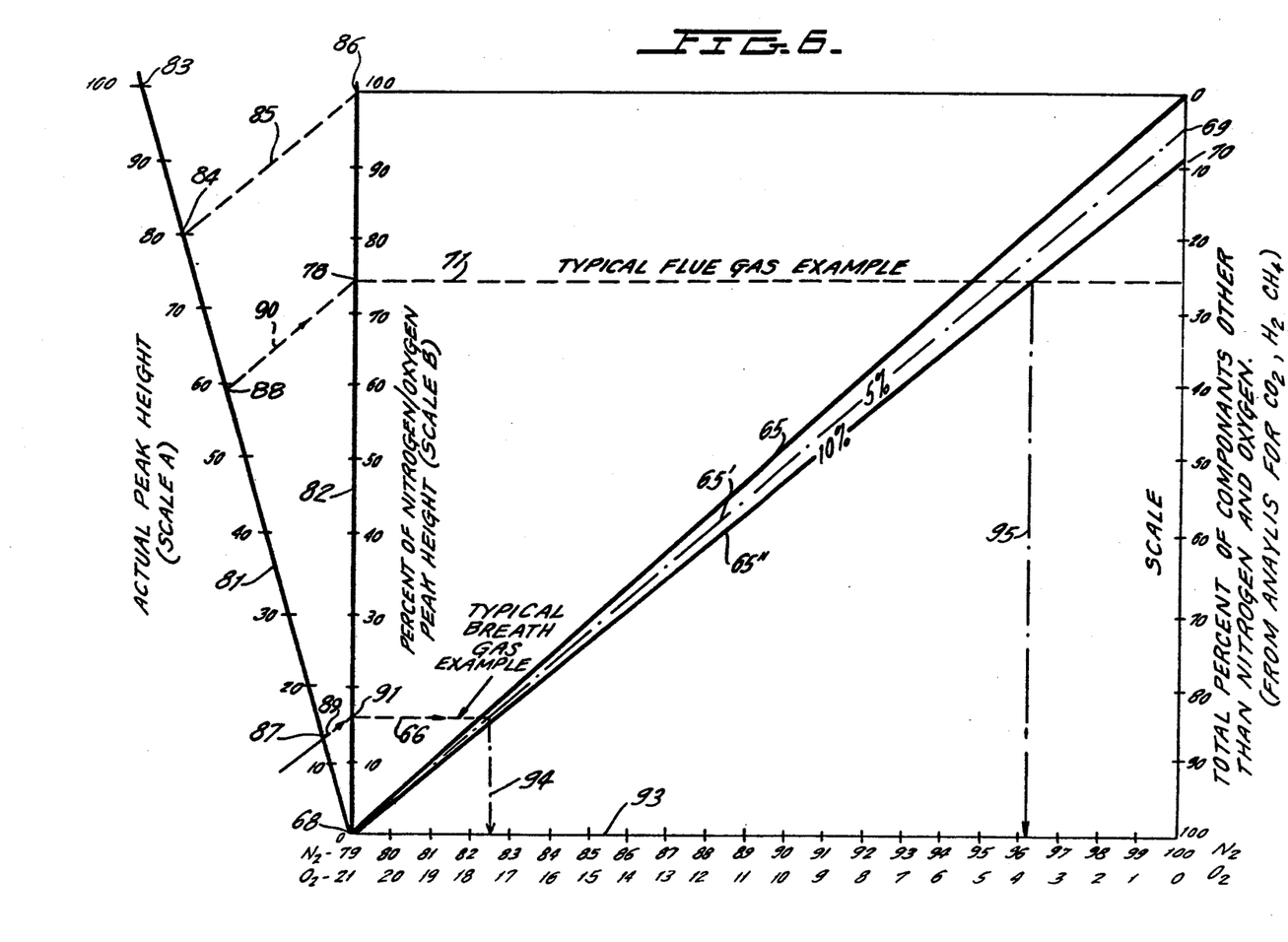
FIG. 6 is an enlarged plot showing the upper right-hand quadrant of FIG. 5 in greater detail.

FIG. 6 is an enlarged plot showing the upper right-hand quadrant of the curve of FIG. 5 in greater detail. Referring to FIGS. 5 and 6, the curve 65 represents the nitrogen/oxygen ratio plotted against peak height of oxygen plus nitrogen, wherein 100 divisions positive represents a ratio of 100% nitrogen to 0% oxygen, and wherein 100 divisions negative represents 0% nitrogen and 100% oxygen. In order to ascertain the actual ratio of the oxygen and nitrogen constituents relative to their combined total and relative to the entire gas sample, the sample is run through the procedural steps set forth hereinabove. The plot or curve obtained (a sample plot being shown, and designated by numeral 70 in the recorder 38). The retention times of the peaks obtained in the plot and their heights establish the constituents present and their concentration in the gas sample.

Let it be assumed in one example that the gaseous sample is typical breath gas, which contains 96% oxygen plus nitrogen and 4% carbon dioxide ($CO_2$). The analysis yields a positive peak for the oxygen-nitrogen concentration when air is employed as the carrier gas.

Let it be assumed that, by proper calibration of the equipment, 100% oxygen plus nitrogen concentration will yield a peak reading of 100 (through the use of an appropriate sample). After calibrating the equipment in this manner and, through the application of typical breath gas, a reading of 16 divisions is obtained. A horizontal dotted line 66 is then drawn on the plot of FIG. 6 and extended to the right until it intersects with curve 65. This indicates that of the total concentration of oxygen plus nitrogen (exclusive of other constituents), nitrogen is present in the amount of 82.3% with 17.7% oxygen being present. To produce the same peak height with a lower percent of oxygen plus nitrogen (since the sample gas contains 4% carbon dioxide), the oxygen deficiency, as compared with air as the carrier, must be greater than 82.3%/17.7%. In order to obtain the actual oxygen/nitrogen ratio, curve 65 is re-drawn as curve 65', which extends from the 0,0 axis (point 68 to point 69 which is four divisions below the maximum scale of 100 divisions), which indicates the presence of 4% carbon dioxide, or a total concentration of 96% oxygen plus nitrogen. Dotted line 66 is then extended further toward the right until it intersects with curve 65', to yield a reading of oxygen-nitrogen in the ratio of 82.6%/17.4%. This ratio must then be multiplied by the fraction of nitrogen plus oxygen in the unknown gas, as determined by the analyses to ascertain the percentage concentration of all other constituents. In the example given hereinabove, the breath gas contains 4% carbon dioxide. Thus, the percentage nitrogen and percentage oxygen are each multiplied by a factor of 0.96 to obtain the actual concentration which is 79.4% nitrogen and 16.6% oxygen. Combined with the percentage concentration of carbon dioxide, this yields a result of 79.4% nitrogen plus 16.6 percent oxygen, plus 4% carbon dioxide, yielding a total of 100.0%.

Considering the analysis of typical flue gas, the percentage concentrations are 10% carbon dioxide and 90% nitrogen plus oxygen. Taking these percentage concentrations into account, the curve 65 is re-drawn as curve 65", extending between the 0,0 axis (point 68) and point 70, which represents a 10% concentration of carbon dioxide or a 90% concentration of oxygen plus nitrogen.

The peak height measured by the analyzer-recorder yields a reading of 74 divisions. A horizontal dotted line 71 is drawn from this point (78) until it intersects with curve 65, yielding a reading of 94.5% nitrogen, and 5.5% oxygen. Since a positive peak is obtained, in order to produce the same peak with a lower percent of oxygen plus nitrogen, the oxygen deficiency must be greater than 5.5%. The actual proportion is thus obtained by extending dotted line 71 until it intersects with curve 65″, yielding a ratio of 96.2% nitrogen and 3.8% oxygen. These proportions are then multiplied by a factor equal to the ratio of the concentration of oxygen plus nitrogen relative to the total gas sample. Thus, the percentages obtained above are multiplied by a factor of 0.9 (since there is 10% carbon dioxide present), yielding an actual concentration of 86.6% nitrogen and 3.4% oxygen, which together with 10.0% carbon dioxide yields a total of 100.0%. Obviously, if other unknown constituents are present, their total percentage subtracted from 100% yields the factor by which the nitrogen/oxygen proportions must be multiplied to obtain their actual percentage concentration.

Curve 65 may also be expressed by the equation $$\% N_2 = 79 + 0.21 \, P.H. \quad (1)$$

or $$\% N_2 = 79 - 0.79 \, P.H. \quad (2)$$

* where P.H. = peak height for $N_2 + O_2$

% $N_2$ = percent of $N_2$ in a mixture of $N_2 + O_2$

*Equation (1) is utilized when a positive peak for the $N_2 + O_2$ reading is detected, while Equation (2) is utilized when a negative peak is present.

For samples which contain other constituents, the following equations should be used:

$$\% N = 79 + \left(\frac{100 - \%y}{21}\right) P.H. \text{ or} \quad (1a)$$

$$\% N = 79 - \left(\frac{100 - \%y}{79}\right) P.H. \quad (2a)$$

where Equation (1a) is utilized when a positive peak for the $N_2 + O_2$ reading is detected and Equation (2a) should be used when negative peaks are detected.

The above examples are given in the case where the electronic gas analysis equipment is calibrated so that 100 divisions exactly equal 100% nitrogen. However, a more simplified procedure may be utilized in which a sample size is selected and an attenuation adjustment is made so as to produce a 100% nitrogen peak which preferably lies in the range from 80 to 100 divisions.

Appropriate adjustment of the attenuator assembly 35 and the coarse and fine adjustment resistors through the knobs 37a and 34a–28b, respectively, together with the analysis of a sample having a known concentration of nitrogen is run through the equipment to obtain a reading wherein the number of divisions provided on the recorder scale represents a concentration of 100% nitrogen. Let it be assumed that this reading is 80 divisions. Making reference to the plot of FIG. 6, a scale line 81, forming an angle of less than 90° with the vertical scale line 82, is drawn from point 68 to a point 83 which may be arbitrarily selected, with the qualification being that the line 81 forms an angle of less than 90° (and preferably less than 45°) with the vertical scale line 82 of the chart. Any suitable point, for example the point 84, may be selected as the point along scale line 81 which represents the actual reading of the recorder for a 100% concentration of nitrogen. A dotted line 85 is then drawn between 84 and the 100 division point 86 along vertical scale line 82 which represents 100% nitrogen concentration. The diagonal line 81 is then divided into 80 equal divisions between point 84 and the zero, zero reference point 68.

Any known mixture of gases may be used to calibrate and obtain the connecting dotted line 85 from the actual peak height scale 81 to the percent of nitrogen-oxygen peak height scale 82. Any unknown peak plotted by the recorder for an unknown sample being analyzed can then be directly transferred to scale 82 from scale 81 by drawing straight (dotted) lines which are parallel to the line 85 which was determined from the known mixture of gases or from a 100% concentration of nitrogen. Thus, considering the examples for typical breath gas and typical flue gas set forth hereinabove in connection with the present example, when 80 divisons represents 100% concentration of nitrogen, then the scale will now read 13 divisions (point 87 along scale 81) and the oxygen-nitrogen concentration in typical flue gas will yield a reading of 59 divisions (represented by point 88 along the actual peak height scale 81). Dotted lines 89 and 90 may then be respectively drawn, which lines must pass through points 87 and 88, respectively, and be parallel to dotted line 85. This technique avoids the need for adjusting the equipment and the sample tube volume to obtain a 100 divisions reading for a 100% nitrogen concentration, which procedure may be rather tedious. Thus, the actual readings may then be utilized to determine the nitrogen and oxygen proportions provided by the curves of FIG. 6. For example, for typical breath gas, the reading of 13 divisions is directly converted into oxygen/nitrogen concentration by dotted line 89 which intersects scale 82 at a predetermined point 91. A horizontal dotted line 66 is then extended toward the right until it intersects the appropriate curve, at which point the hydrogen plus oxygen ratio may be read from the horizontal scale 93. In a like manner, an actual peak reading of 59 divisions plotted along scale 81 is converted into an oxygen/nitrogen concentration ratio by drawing the dotted line 90 from point 88 parallel to dotted line 85 until it intersects the vertical scale line 82. At this point, a horizontal line (line 71) is drawn and extended toward the right until it intersects with the appropriate curve, thereby enabling the nitrogen plus oxygen ratio to be read from the horizontal scale 93 (i.e., the point along scale 93 at which phantom line 95 intersects with scale 93). A similar phantom line 94 is drawn downwardly from the point at which dotted line 66 intersects the appropriate curve to indicate the nitrogen plus oxygen ratio reading derived from horizontal scale 93. Equations (1) or (2) may be employed in this technique, whereby peak values are simply proportioned first before solving for actual concentrations of $N_2$ and $O_2$.

Figures 7, 7A, 8:
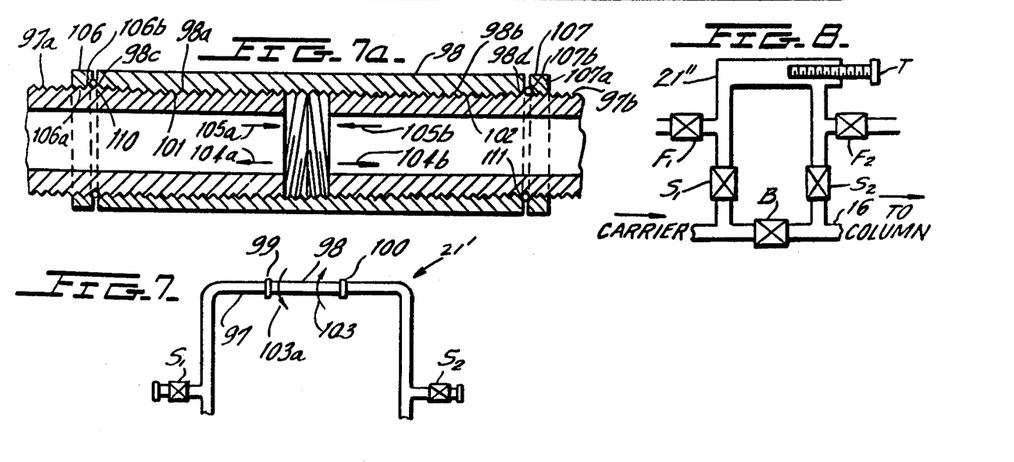
FIGS. 7 and 8 are schematic diagrams of alternative sample tube arrangements.

Another technique which may be employed to obtain readings from the recorder wherein 100 divisions exactly equals a 100% nitrogen concentration is through the use of the sample tube assembly 21′, shown in FIG. 7. The sample tube assembly 21′ of FIG. 7 is modified as compared with the sample tube 21 shown in FIG. 2, in that the assembly has a substantially square-looped configuration. Only that much of the sample tube assembly 21′ has been reproduced in FIG. 7 so as to understand the manner in which it replaces sample tube 21 of FIG. 2 (Note its connection with the valve assemblies $S_1$ and $S_2$, shown in FIG. 7.

The sample tube assembly is substantially U-shaped and has a central arm portion 97 and adjustable members 98, 99 and 100 which operate to adjust the volume of the sample tube assembly 21′, as will be best understood from a consideration of FIG. 7a which shows a detailed sectional view of the central portion 97. As shown in FIG. 7, central portion 97 is comprised of first and second arms 97a and 97b, each of which are threaded along their exteriors, as shown at 101 and 102, respectively. The threaded portions 101 and 102 are of reverse directions, for a purpose to be more fully described. Rotatable member 98 is tapped along its interior left-hand portion 98a so as to threadedly engage threaded portion 101, while the right-hand interior portion 98b is tapped so as to threadedly engage the threaded portion 102. The reverse directions of the threaded and tapped portions is such that when member 98 (which preferably has a knurled exterior surface) is rotated in a first direction, as shown by arrow 103, the tubular portions 97a and 97b move away from one another, as shown by arrows 104a and 104b, respectively. In order to assure air-tight sealing of the sample tube assembly, lock nuts 106 and 107 are provided. These nuts have their interior surfaces 106a and 107a tapped so as to threadedly engage with threaded portions 101 and 102, respectively. The outer ends of member 98 are beveled at 98c and 98d, while the mating surfaces of members 106 and 107 are beveled at 106b and 107b, respectively, so as to firmly engage O-rings 110 and 111, respectively, in order to air-tightly seal the sample tube assembly.

By rotating knurled member 98 in the reverse direction, as shown by arrow 103a in FIG. 7, tubular portions 97a and 97b move toward one another in the directions shown by arrows 105a and 105b, respectively.

Adjustment of the sample tube volume is preferably carried out by first loosening the lock nuts 106 and 107 to permit member 98 to be freely rotated by appropriate rotation of member 98. The arms 97a and 97b, which member 98 threadedly engages, are moved either toward one another or away from one another so as to change the interior volume of the sample tube assembly. After appropriate adjustment, the lock nuts 106 and 107 may be rotated so as to firmly compress to O-rings 110 and 111 and thereby air-tightly seal the assembly. As an alternative embodiment, in instances where a sufficient air-tight seal is employed in applications where the operating pressures of the system are low, members 106 and 107 and O-rings 110 and 111 may be eliminated. As a further alternative, not only may members 106, 107, 110 and 111 be eliminated, but the threaded and tapped portions of members 101-102 and 98 may be respectively eliminated and member 98 may be replaced by a flexible, resilient tube such as, for example, a rubber tube which is fitted over tubular portions 97a and 97b so as to form a force-fitting coupling therebetween. Thus, by pulling one or both of the tubular portions 97a or 97b in the directions shown by arrows 104a, 104b, 105a and 105b, the volume of the sample tube may thus be adjusted so as to provide additional means for adjusting the scale reading of the recorder to obtain a reading of 100 divisions for a 100% nitrogen concentration or to obtain any other desired scale reading.

As another alternative, the arrangement of FIG. 8 may be employed wherein the sample tube 21" is provided with a tapped opening cooperating with threaded member T which may be inserted to a greater or lesser depth into the tube interior simply by rotating member T in a first or a second direction.

The head of threaded member 9 may be conveniently mounted along the front face of the control panel as shown in FIG. 2A. The head may be provided with a pointer for alignment with a stationary scale S to facilitate accurate adjustment of the sample volume to assure accurate repetition of earlier test runs. A moving vernier scale V (movable with rotation of the head of screw T), positioned behind an annular shaped window may be employed for still further accuracy in obtaining a precise volume reading.

It can, therefore, be seen from the foregoing description that the present invention provides a novel automatic and electronic gas analyzer in which qualitative and quantitative analyses of constituents in a gas sample may be readily and accurately determined, as well as providing a novel method and apparatus for determining nitrogen and oxygen concentrations in a gas sample through the use of air as a carrier gas.

Although this invention has been described with respect to its preferred embodiments, it should be understood that many variations and modifications will now be obvious to those skilled in the art, and, therefore, the scope of this invention is limited not by the specific disclosure herein, but only by the appended claims.

The embodiments of the invention in which an exclusive privilege or property is claimed are defined as follows:

1. A method for determining the percent concentration of oxygen and nitrogen in a gas sample provided within a storage container and having unknown quantities of nitrogen and oxygen, which method employs air as a carrier gas, comprising the steps of:
   (a) adjusting a bridge circuit having filaments in two arms of said bridge, said filaments having conductivities which vary as a function of the constituents in the gas passing therethrough, so that the output signal of the bridge circuit is null when the bridge circuit is balanced:
   (b) limiting the maximum magnitude of the output signal developed by the bridge circuit as a result of the most extreme unbalanced condition measureable by the bridge circuit, and identifying said magnitude as having an arbitrary value of 100 units;
   (c) passing the gas sample from the storage container through a separating column containing an adsorptive material using air as a carrier which is injected into the storage container at a predetermined pressure;
   (d) passing the mixture of the sample gas and air emitted from the output of the columm over a first filament of said bridge circuit;
   (e) simultaneously passing the air directly from its source over the remaining filament of the bridge circuit so as to generate a substantially continuous signal which is representative of the ratio of conductivities of said first and second filaments whose peak value at a predetermined time interval represents a concentration of $N_2 + O_2$ and whose polarity represents the deficiency of nitrogen or oxygen relating to the concentration of nitrogen and oxygen in air, a positive polarity peak relative to a reference level representing a percentage of oxygen in the gas sample of less than 21/100 and a negative polarity peak relative to the reference level representing a percentage of oxygen in said gas sample of greater than 21/100;
   (f) determining the exact percentage ratio of nitrogen in the nitrogen plus oxygen constituents of the gas sample by increasing 21% of the peak value of the signal occurring at the aforesaid predetermined time interval by 79 units.

* * * * *

UNITED STATES PATENT AND TRADEMARK OFFICE
CERTIFICATE OF CORRECTION

PATENT NO. : 4,100,790
DATED : July 18, 1978
INVENTOR(S) : Gerald J. Harvey

It is certified that error appears in the above-identified patent and that said Letters Patent are hereby corrected as shown below:

Column 4, Line 56, the word "obtained" should read --determined--

Column 8, Line 6, after the word "shown" insert --in Figure 2--

*Signed and Sealed this*

*Twentieth* Day of *March 1979*

[SEAL]

Attest:

RUTH C. MASON
*Attesting Officer*

DONALD W. BANNER
*Commissioner of Patents and Trademarks*